US006255652B1

United States Patent
Moyer

(10) Patent No.: US 6,255,652 B1
(45) Date of Patent: Jul. 3, 2001

(54) METHOD AND APPARATUS FOR DETECTING INSECT INFESTATION IN ENCLOSED AREAS

(76) Inventor: William T. Moyer, P.O. Box 117, Long Beach, NC (US) 28465

( * ) Notice: Subject to any disclaimer, the term of this patent is extended or adjusted under 35 U.S.C. 154(b) by 0 days.

(21) Appl. No.: 09/312,153

(22) Filed: May 14, 1999

(51) Int. Cl.[7] .................................................. G01N 21/34
(52) U.S. Cl. .......................... 250/343; 250/338.1; 356/51
(58) Field of Search ............................... 250/343, 338.1, 250/338.5, 352; 356/51

(56) References Cited

U.S. PATENT DOCUMENTS

| 3,963,927 | 6/1976 | Bruce et al. | 250/338 |
| 4,206,353 | 6/1980 | Delgrosso | 250/343 |

FOREIGN PATENT DOCUMENTS

| 1245646 | * 3/2000 | (CN) | A01N/25/18 |

OTHER PUBLICATIONS

"Detection of Hidden Insect Infestations in Wheat by Infrared Carbon Dioxide Gas Analysis" By William A. Bruce et al, U.S. Department of Agriculture, AAT–S–26/Jul., 1982.

* cited by examiner

Primary Examiner—Constantine Hannaher
Assistant Examiner—Otilia Gabor
(74) Attorney, Agent, or Firm—Michael E. Mauney

(57) ABSTRACT

Method and apparatus for detecting insect infestation within enclosed wall areas by detecting increased concentrations of a tell-tale gas. An intake nozzle is connected to an infrared gas analyzer by tubing and a pump. Ambient air in a room where an insect infestation in a wall is suspected is first sampled. A baseline gas reading is obtained. A small hole is made in the area of the wall where an insect infestation is suspected. The intake nozzle is placed within the hole and a second gas sample is taken. Concentration of the tell-tale gas in the second sample is compared to the concentration in the gas of the first ambient air sample. An increased concentration will ordinarily indicate presence of an insect infestation in the suspected area In most applications the tell-tale gas is $CO_2$.

9 Claims, 3 Drawing Sheets

METHOD AND APPARATUS FOR DETECTING INSECT INFESTATION IN ENCLOSED AREAS

FIELD OF INVENTION

This invention relates to apparatus and methods for detecting insect infestation and, more specifically, termite infestation within an enclosed area

BACKGROUND OF INVENTION

Insect infestations and the damage they cause are as old as human history. One of the seven plagues visited on Egypt by God in the Old Testament is a locust infestation. An unchecked insect pest, such as a fruit fly, can destroy an entire agricultural industry in an area The whole face of the south was changed in the early part of the twentieth century by the boll weevil and its impact on cotton farming.

Because of natural predators, many insects will try to remain hidden. Detection by ordinary as visual means may be difficult, if not impossible. Therefore, for imported food or other natural materials, quarantines of the imported material are sometimes required or even irradiation or sterilization.

Like all other animals, insects inspire oxygen and respire carbon dioxide ($CO_2$). However, $CO_2$ gas is present in the atmosphere in large quantities, Therefore, the quantity of $CO_2$ produced by an individual insect is difficult to detect in the presence of naturally occurring $CO_2$ because of the variations that are normal within a $CO_2$ concentration in a particular area Not only insects produce $CO_2$, but internal combustion engines, other animals, and other chemical operations that use carbon may also produce $CO_2$. Therefore, even fairly substantial infestations of insects do not ordinarily produce enough $CO_2$ to make detection possible. While it may be possible to use a slow long-term test that establishes a base line, this is not effective for most applications.

Consequently, it has been recognized that it can be useful to use infrared carbon dioxide gas analysis to detect hidden insect infestations. Two systems have been proposed to use infrared analysis of carbon dioxide to detect hidden insect infestations. In Bruce et al., U.S. Pat. No. 3,963,927, a system for detecting respired $CO_2$ is disclosed. Here, a sample of the materials in which an insect infestation is suspected is sealed in a chamber. The air inside the chamber is held stable for an interval of time then moves through the system as a plug flow or bolus through an infrared analyzer. The sample chamber in which the material to be tested is placed is first purged with a carrier gas and then sealed off for a long enough time to allow respired $CO_2$ by insects contained within the sample material to build up and reach a concentration sufficient for detection. It is this gas which is analyzed for higher $CO_2$ concentration and compared to the earlier carrier baseline gas.

Delgrosso, U.S. Pat. No. 4,206,353, also discloses a system for detecting live insects in a commodity. This invention, like the Bruce et al Patent, uses a closed chamber with an incubation time and a purge by a base line or reference gas. Outside air is used as a reference to compare against air from within the closed chamber where the presumed sample has incubated, hence, allowing any insects contained within the sample to respire sufficient carbon dioxide within that sample for detection by an infrared detection device.

These devices, while useful, especially for commodity products like wheat or rice that can be easily sampled, cannot be used to detect insects in many applications where detection is important. These devices require a sealed chamber as part of the device to allow a controlled increase in the $CO_2$ concentration in the chamber for detection. This means the product where an insect infestation is suspected must be like wheat or rice that are easily sampled for testing in a sealed chamber.

SUMMARY OF THE INVENTION

It is the current object of the present invention to provide a simple, easy, and non-destructive method for testing for insect infestation, primarily termite infestation, within the walls of a house. Under current building practices, most houses are built of wood frames. Ordinarily, an outside siding material is mounted against plywood or particle board sheathing secured to the wood frames. Within the spaces between the frames, insulation is placed. Between the wooden sheathing and outside siding, a wrap or vapor barrier is placed. This construction practice provides that there is very little ambient air movement from the outside to within the spaces between the wooden framing members. Movement of the air in this area is further restricted by the fiberglass insulation bats or other insulation material that is placed between the wooden framing members. Inside the house there is drywall, paneling, or wall board mounted against the wooden framing members, which is then painted or finished according to the taste of the homeowner.

In a building where termite infestation is suspected, one may visually inspect the foundation for evidence of termite infestation. If this is found, further investigation may be required. However, there is no easy way to investigate which part of the wall joists have been infested by termites and which part have not without tearing away the wall to visually examine the wood that is underneath. This is a destructive and expensive procedure. Consequently, it would be an advance in the art to use respired $CO_2$ from insects, usually termites, with a carbon dioxide detector to see whether a particular area underneath a wall is infested by live termites or other insects without destroying any substantial portion of the wall The vapor barrier wrap, the sheathing, and the wall material, in effect, turns each of the areas between each section of the supporting framing into a sealed detection chamber. There is very little motion of ambient outside air into this area. The current invention proposes the following means of detecting termite infestation in this area First, there is a pump connected to an intake nozzle. The pump will pull air in through the intake nozzle and to an infrared carbon dioxide detector. For detection to take place, the operator will first activate the pump within a room in a house to obtain a background baseline reading. Once this reading is obtained, the pump will be turned off. The intake nozzle will be inserted through the wall material into an area between the wall framing. The intake pump will then again be activated. Ordinarily, there will be a rubber seal or other material at the base of the intake nozzle. This seals the intake nozzle from taking in room air. The intake nozzle itself may consist of the type of hollow needle like that used to inflate sporting items like footballs or basketballs. Only a small hole need be made in the wall material for insertion of this type of intake nozzle. Once the nozzle is in place, the intake pump is again activated so that the interior air behind the wall board and between the wood frames will be pulled into the infrared $CO_2$ analyzer in a plug flow fashion. After sufficient time has elapsed to allow the analyzer to be detecting the air from within the appropriate area in which an insect infestation is suspected, an output reading is noted and compared against the earlier baseline reading of $CO_2$ found in the room. It has been found in practice that an increase of several parts per million indicates a likely insect infestation in that area of the framing. At that point, further investigation will be warranted, including possible destruction of a portion of the wall material so that a visual inspection of the area may be made.

It has been found in practice that this procedure is accurate and greatly reduces the amount of damage done to a building to determine if there is a termite infestation. Further, this type of apparatus and method can be made from existing materials and equipment, is portable, lightweight, easy to operate, may be powered by batteries, and can be made at a cost that makes it practical to use for those in the business of insect infestation detection and repair.

DETAILED DESCRIPTION OF THE DRAWINGS

Figure 1:
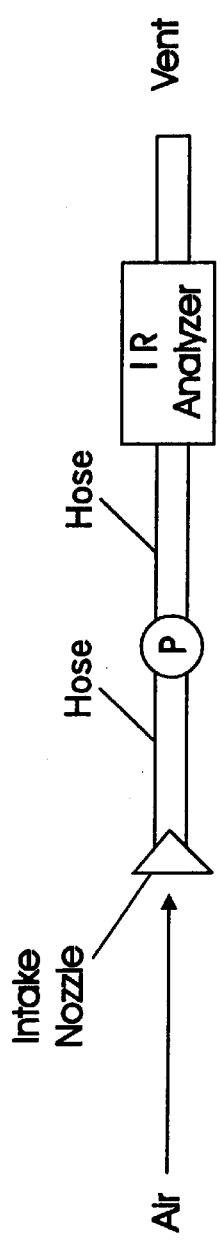
FIG. 1 shows a schematic diagram of the invention.

FIG. 1 is a schematic diagram of the invention. At one end of the invention is an air intake nozzle. It is connected to an infrared analyzer. The infrared analyzer samples the air coming from the intake nozzle. Analyzed air escapes from the system through a vent. Ordinarily, the device will require some way of moving air from the intake nozzle across the infrared analyzer. This ordinarily will be a pump. In FIG. 1 the pump (P) is shown positioned between the intake nozzle and the infrared analyzer and connected to each by flexible airtight hoses. However, this arrangement is a matter of convenience. The device could be made of one piece with the intake nozzle appearing like a shank of an ice pick or a screwdriver, having a hollow interior bore, leading to an infrared analyzer with a pump to move the air. In such a one-piece device, one could simply pierce the siding of a wall to be examined with a sharp end of the intake nozzle, then activating the pump to pull air through the intake nozzle and across the infrared analyzer. For the device to operate effectively, it only requires that air being pulled through the intake nozzle be segregated from ambient air. This assures the air being sampled and analyzed will have increased $CO_2$ concentration in the event of a hidden insect infestation.

The current invention will ordinarily operate in two stages. The first stage obtains a baseline $CO_2$ rating. In the first stage ambient air is sampled within a room or in the vicinity of a suspected termite infestation. The second stage samples an enclosed, confined area where the termite infestation is suspected. Air coming through the intake nozzle is analyzed by the infrared analyzer and this reading is compared to the baseline $CO_2$ reading for the ambient air analyzed in stage 1. An increased $CO_2$ reading above the baseline reading is an indication of an active insect infestation within the enclosed area being sampled in stage 2.

Figure 2:
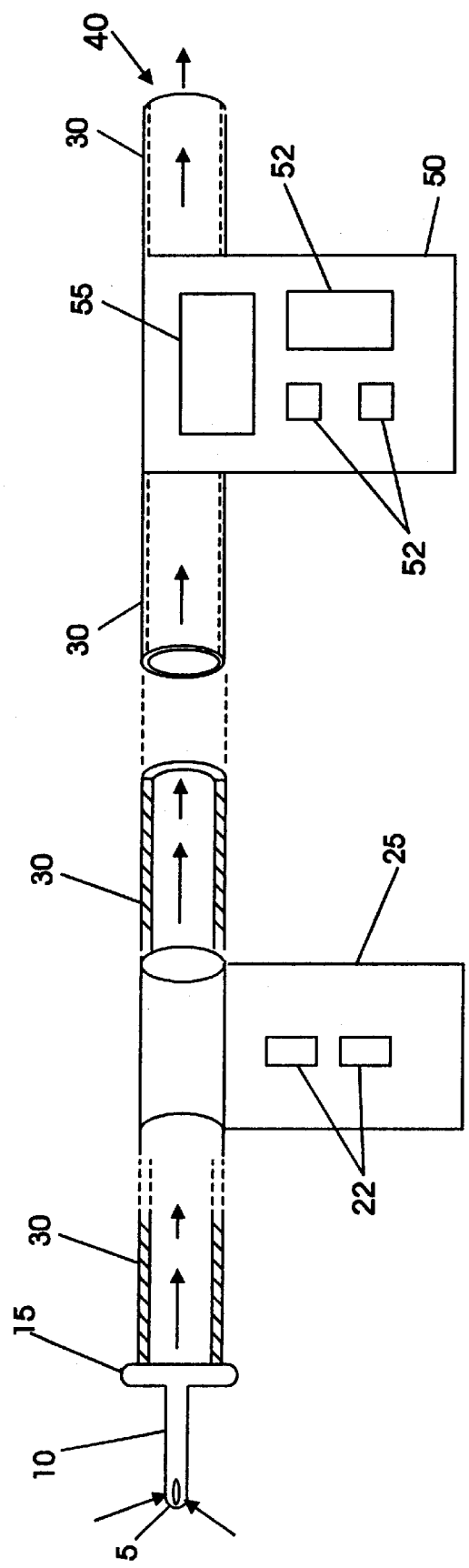
FIG. 2 shows the invention in more detail.

FIG. 2 shows a practical embodiment of the invention in detail At one end is the intake nozzle (10). This consists simply of a straight cylindrical-like hollow needle with an air intake opening (5) at the end of the intake nozzle (10). In practice, it has been found that the type of hollow needle used to inflate basketballs or footballs will work very well. This is a rigid, small diameter, hollow needle with openings at one end and a threaded base. The threaded base is easily removably connected to the type of hollow rubber hose used for bicycle pumps or other types of common air pumps. At the base of the intake nozzle (10) is a rubber gasket (15). In operation a hole with a bore approximately the same as the bore of the intake nozzle (10) is made in wallboard, dry wall, paneling, or the wall material where the infestation sample is to be taken. The intake nozzle (10) is pressed through the hole in wallboard, paneling, or the like with the gasket (15) pressed tightly against the wall surface. In many applications the gasket (15) will not be required. If the hole in the wall material is close to the size of the intake nozzle, then a snug fit of the intake nozzle against the wallboard, dry wall or paneling would be enough to prevent outside ambient air from being pulled, along with the air being sampled in the confined space, across the infrared analyzer, thus, affecting the accuracy of the reading. However, the gasket (15) will help prevent ambient air, outside of the enclosed space to be sampled, from being drawn into the intake opening (5) by the action of the pump (25). The pump (25) is connected to the intake nozzle (10) by a hollow flexible hose (30) shown in a cut-a-way in the first part of FIG. 2. Air flow through the invention is indicated by the arrows to the intake opening (5) and inside the hose (30). The pump (25) pulls air through the intake opening (5) down the bore of the intake nozzle (10) through the hose (30) and pushes it onward to the infrared analyzer (50). Not all of the hose (30) is shown in FIG. 2. The dotted lines in FIG. 2 indicate a length of the hose (30) that is not shown. There is an output screen (55) on the infrared analyzer (50) which gives a read-out of the $CO_2$ concentration from the sample taken.

Because gas detection is important in many applications, a wide variety of commercially available pumps and infrared analyzers are available on the marketplace. It has been found in practice that the "Smart Pump" manufactured Draeger Safety, Inc. will work well as the pump (25) shown in FIG. 2. This pump is lightweight, battery operated, and is possible to clip onto the belt. The operation of the pump (25) is controlled by switches (22) on the pump (25). It pumps between 0.2 and 0.9 liters of air per minute and is powered by four AA alkatine cell batteries. However, any battery operated pump with the appropriate pumping volume will work as well.

It has been found also that a variety of infrared analyzers to analyze for $CO_2$ concentration are commercially available. It has been found in practice that a PAC III single gas instrument manufactured by Draeger Safety Inc. of Pittsburgh, Pa. with a $CO_2$ sensor will work well. This instrument is approximately 4.3×2.6×1.3 inches in size, weighs 7 ounces, and uses a 9 volt alkaline battery, although rechargeable nickel cadmium or lithium batteries may also be used. It uses a LED display for the output screen (55) and can be set to give both visual and audible alarms, as well as a low battery alarm. The operation of the infrared analyzer (50) is controlled by the buttons (52) in the front of the infrared analyzer (50). The PAC III single gas detector may be equipped with a number of different gas detection modules. This enables it to be used not only for detection of increased $CO_2$ concentrations, but other gases such as methane, carbon monoxide, and the like. Thus, this invention could be used to test for increased concentrations of gases that may be characteristic of insect infestation other than $CO_2$. For example, it has been suggested that methane may be used to detect insect infestation. Also, other types of gases could be trapped within the wall spaces and tested for using the apparatus and methods of this invention. Under some circumstances, such gases as radon, carbon monoxide, or other toxic gases could be tested for, using this invention to help detect or localize sources responsible for production of those gases. While it is believed this invention will find its widest use in detection of termite infestations by carbon dioxide, that is not the sole use envisioned by the inventor. Increased concentrations of any detectable gas in the space between the wall studs may be discovered by use of this invention.

Figure 3A:
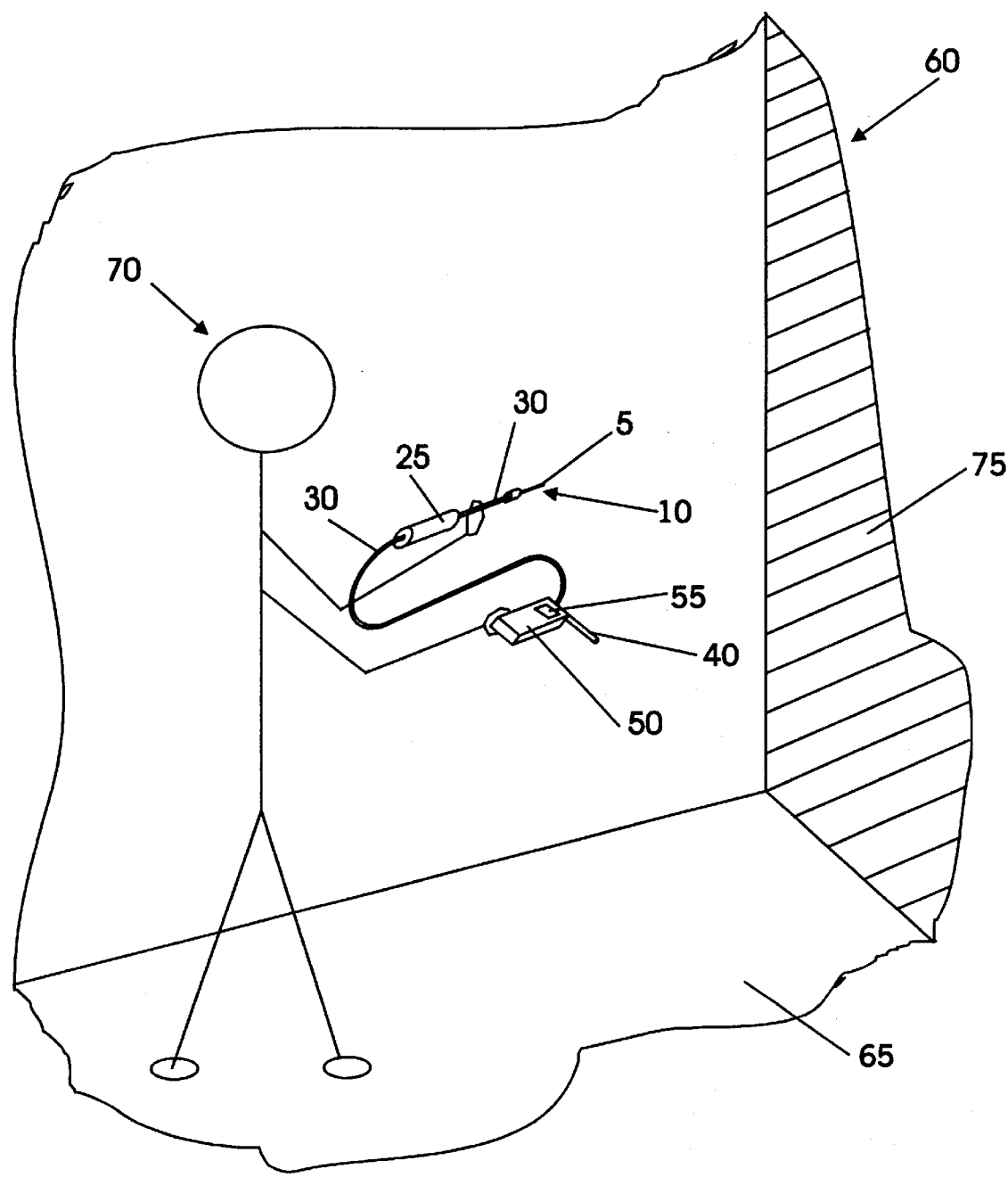
FIGS. 3A and 3B show the invention in operation in a building.

FIG. 3A shows an operator (70) inside a cut-a-way room. He is standing on the floor (65) in proximity to a wall (60) covered with a wallboard material (75). There is a suspected termite infestation in the wall (60). The operator (70) will activate the pump (25) which will begin to pull air into the intake nozzle (10) through the intake opening (5). The ambient air inside the room passes through the flexible hose (30) and across the detector module on the infrared analyzer (50). A continuous reading is shown on the output screen (55). Most commercial carbon dioxide analyzers allow one to obtain a reading in carbon dioxide parts per million in the atmosphere. One may also adjust the reading so that a baseline reading is zero by use of a standard gas sample. If the standard gas sample is used to establish a baseline reading of zero, then the reading within the room will ordinarily be a few parts per million above or below zero. One operates the pump (25) until a steady reading is obtained on the infrared analyzer (50). This establishes the baseline $CO_2$ concentration for the room in which the reading is to be taken.

Figure 3B:
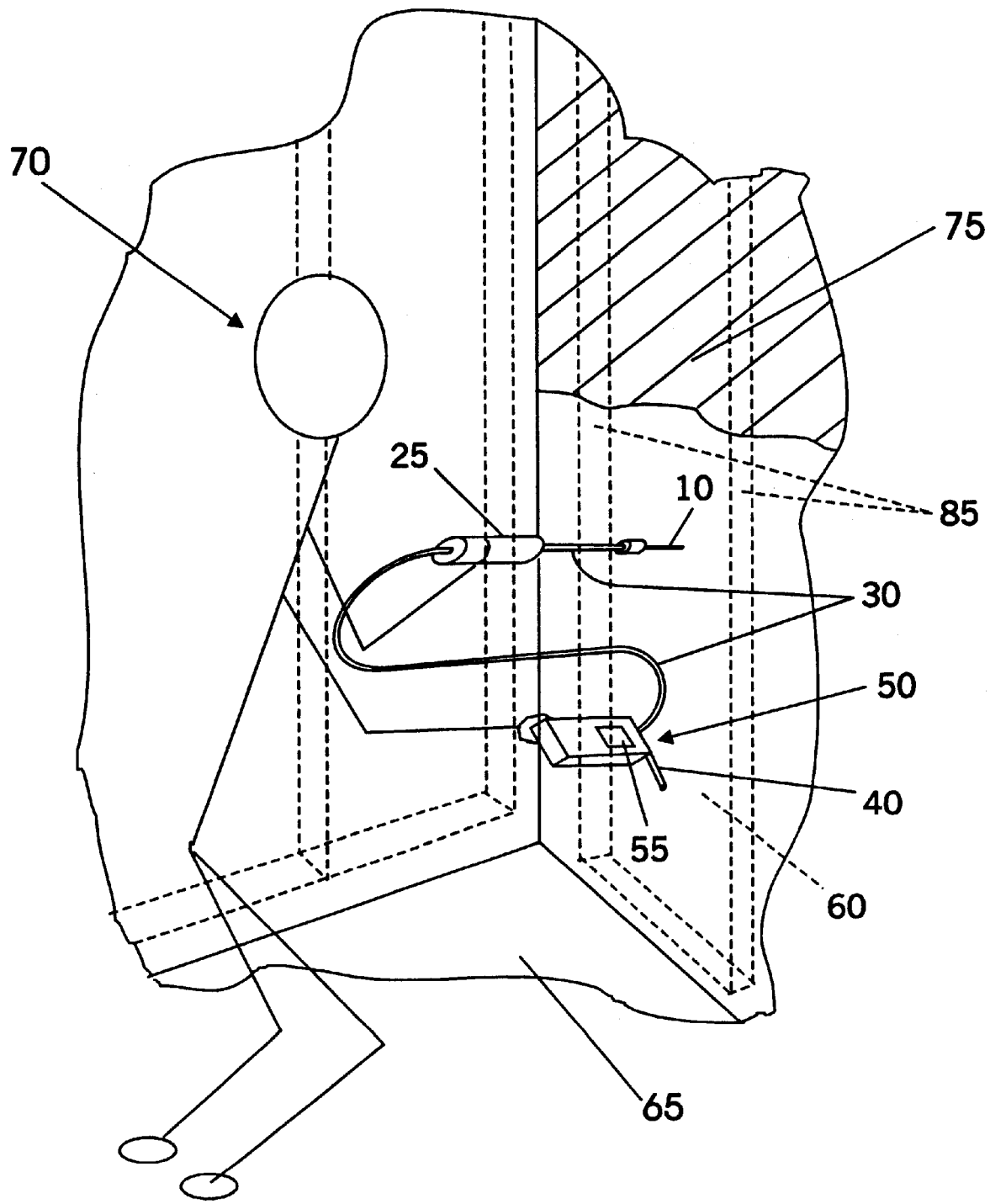

FIG. 3B shows the reading actually being taken. Ordinarily, a small punch-like tool (not shown) will be employed to punch a small hole in the wall board material (75). Ordinarily, this will be wallboard or paneling. The hole punched by the punch device will be slightly larger than the intake nozzle (10). One must be sure that the hole is between the studs (85) and not within a stud. This is ordinarily a simple matter to determine by the feel of the punch device as it passes through the wallboard material (75) and into what should be the hollow interior behind the wall covering. In FIG. 3B, a portion of the wall board material (75) is shown cut-a-way for better showing the position of the intake nozzle (10) between the studs (85). The intake nozzle (10) is passed then through the hole made by the punch device and secured against the wall board material (75) to avoid ambient air from outside of the room being sucked into the intake nozzle (10). A rubber gasket (not shown) is securely pressed against the wall covering material, be it siding or wallboard. The pump (25) is activated. Air begins to pass down the flexible hose (30). Ordinarily, the air flow will be in a bolus or plug flow fashion. This means that ambient air is still within the flexible hose (30) and the initial reading obtained on the infrared analyzer (50) will not change until the ambient air present in the flexible hose (30) is entirely pushed through the tube by the pump and out of the end of the flexible hose's (30) outlet (40). During this process, the user (70) observes the output screen (55) on the infrared analyzer (50). While the ambient air is passing over the carbon dioxide detector module the reading on the output screen (55) should not change. However, as the plug flow bolus of the air being withdrawn between the studs (85) of the wall (60) pass over the infrared analyzer (50), the output screen (55) will change if there is an increased carbon dioxide in the area being sampled. If the output reading increases by two or three parts per million, this is a positive result indicating that insect infestation is in the wall and further investigation is warranted. Many infrared analyzers (50) have a computer chip or some other memory means within their circuitry which will record highest and lowest readings and be shown to the user (70) on the output screen (55) by use of the buttons (52) (not shown in FIG. 3b) on the infrared analyzer (50). This means that the user (70) need not observe the output screen (55) constantly, but that high or low readings will be automatically recorded and available for review. However, in most circumstances, the observer will be closely watching the output screen (55) once he has activated the pump (25) while the intake nozzle (10) is inserted in the area to be sampled.

What is claimed is:

1. An apparatus for detecting relative concentrations of a gas in an enclosed space comprising:
   (a) means for sampling for gas in an open space and in an enclosed space between wall studs behind a wall;
   (b) means for analyzing relative concentrations of a gas;
   (c) means for pumping gas from said gas intake nozzle to said means for analyzing relative concentrations of a gas.

2. An apparatus for detecting relative concentrations of a gas in an enclosed space of claim 1 wherein said means for pumping is a pump and tubing for connecting said pump to said means for sampling and said pump to said means for analyzing relative concentrations of gas.

3. An apparatus for detecting relative concentrations of a gas in an enclosed space of claim 2 wherein said means for detecting is an infrared gas analyzer.

4. An apparatus for detecting relative concentrations of a gas in an enclosed space of claim 3 wherein said infrared gas analyzer detects increased concentrations of $CO_2$ indicating presence of a $CO_2$ source in said enclosed space between wall studs.

5. An apparatus for detecting relative concentrations of a gas in an enclosed space of claim 4 wherein said means for sampling is a gas intake nozzle.

6. An apparatus for detecting relative concentrations of a gas in an enclosed space of claim 5 wherein said gas intake nozzle is a small hollow needle whereby said needle's shaft is at least one-half inch long.

7. A method for detecting hidden insects between wall studs in an enclosed wall area in a building comprising:
   (a) detecting the ambient concentration of $CO_2$ in the air in a building;
   (b) making a small hole in the wall of a building between studs in a wall of said building;
   (c) placing an intake nozzle within said small hole;
   (d) withdrawing air from the inside of a wall between studs through an intake nozzle and transmitting it to a gas analyzer;
   (e) measuring the $CO_2$ content of said air with a gas analyzer;
   (f) comparing the $CO_2$ concentration obtained in step (a) to the $CO_2$ concentration obtained in step (e) to determine if there is an increased amount of $CO_2$ in the trapped air between the studs inside the wall as compared to the ambient air in the room.

8. A method for detecting hidden insects between wall studs in an enclosed wall area in a building of claim 7 further comprising said step of measuring the $CO_2$ content of said air is performed by an infrared $CO_2$ gas analyzer.

9. A method for detecting hidden insects between wall studs in an enclosed wall area in a building of claim 8 further comprising said step of withdrawing air from the inside of a wall between studs through an intake nozzle and transmitting it to a gas analyzer is performed by a battery powered pump.

* * * * *